United States Patent [19]

Duffett

[11] Patent Number: Plant 5,618

[45] Date of Patent: Dec. 31, 1985

[54] CHRYSANTHEMUM PLANT NAMED SIREN

[75] Inventor: William E. Duffett, Salinas, Calif.

[73] Assignee: Yoder Brothers, Inc., Barberton, Ohio

[21] Appl. No.: 574,689

[22] Filed: Jan. 27, 1984

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Siren particularly characterized as to uniqueness by the combined characteristics of flat capitulum form; daisy capitulum type; deep orange ray floret color; diameter across face of capitulum ranging from 7 to 8 cm. at maturity; uniform seven to eight week photoperiodic flowering response to short days; short plant height when grown as a pinched spray pot mum; semi-spreading branching pattern; tolerance of both low winter 13° C. and high summer 24° C. to 38° C. temperatures for bud initiation and flower development.

3 Drawing Figures

The present invention comprises a new and distinct cultivar of *Chrysanthemum morifolium, Ramat.*, named Siren.

Siren is a product of a planned breeding program which had the objective of creating new chrysanthemum cultivars for pinched spray pot mum programs having daisy capitulum type, orange floret color, eight week flowering response and the ability to produce commercially acceptable quality in year round programs. Such traits in combination were not present or needed improvement in previously available commercial cultivars.

Siren was originated from a cross made in a controlled breeding program in Salinas, Calif. in 1979. The female parent was an unnamed seedling identified as 78113002, originated by the present inventor from a hybridization of two unnamed seedlings. The male parent of Siren was an unnamed seedling identified as 79121007, originated from a cross between an unnamed seedling and Circus, disclosed in U.S. Plant Pat. No. 4,188.

Siren was discovered and selected as one flowering plant within the progeny of the stated cross by William E. Duffett in March 1980 in a controlled environment in Salinas, Calif.

The first act of asexual reproduction of Siren was accomplished when vegetative cuttings were taken from the initial selection in June 1980 in a controlled environment in Salinas, Calif. by a technician working under formulations established and supervised by William E. Duffett. Horticultural examination of selected units initiated October 1981 has demonstrated that the combination of characteristics as herein disclosed for Siren are firmly fixed and are retained through successive generations of asexual reproduction.

Siren has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Siren which in combination distinguish this chrysanthemum as a new and distinct cultivar:

(1) Flat capitulum form.

(2) Daisy capitulum type.

(3) Deep orange ray floret color.

(4) Diameter across face of capitulum ranging from 7 to 8 cm. at maturity.

(5) Uniform seven to eight week photoperiodic flowering response to short days.

(6) Short plant height (requiring 2 long day weeks prior to pinch followed by 3 to 7 long days prior to short days, and 0 to 1 application of 2500 ppm B-9 SP in 7 to 14 days after the beginning of short days to attain a flowered plant height of 25 to 35 cm. in 6" pots).

(7) Semi-spreading branching pattern.

(8) Tolerance of low winter 13° C. temperature.

(9) Tolerance of high summer 24° C. night to 38° C. day temperatures for bud initiation and flower development.

The accompanying photographic drawings depict typical leaf and inflorescence characteristics of Siren. Sheet 1 is a color photograph of a plant of Siren grown as a pinched spray pot mum, with colors being as accurate as possible with renditions of this type. Sheet 2 is a black and white photograph of three views of the inflorescence of Siren. Sheet 3 shows the leaves of Siren in three stages of growth (mature, intermediate, immature).

Of the many commercial cultivars known to the present inventor, the most similar in comparison to Siren is Cirbronze, disclosed in U.S. Plant Pat. No. 4,492. Reference is made to attached Chart A which compares certain characteristics of Siren to those same characteristics of Cirbronze.

Similar traits are the capitulum form, type and semi-spreading plant habit. Siren has a shorter plant height, faster response time, superior tolerance of both high and low temperatures for bud initiation and development, larger diameter across face of capitulum, and more orange, less red in the ray floret color.

In the following description, color references are made to The Royal Horticultural Society Colour Chart. The color values were determined between 10:30 A.M. and 10:45 A.M. on Dec. 1, 1983 under 150 foot-candle light intensity at Salinas, Calif.

Classification:

*Botanical.*—*Chrysanthemum morifolium, Ramat.*, cv Siren.

*Commercial.*—Daisy spray pot mum.

I. Inflorescence:

A. *Capitulum.*—Form: Flat. Type: Daisy. Diameter across face: 7 to 8 cm.

B. *Corolla of ray florets.*—Color (General tonality from a distance of three meters): Deep orange. Color: (abaxial): Close to 169A oxidizing to 34B, but not accurately depicted in the color chart. Color (adaxial): 168B-C. Shape: Oblong. Rounded tip.

C. *Corolla of disc florets.*—Color (mature): 151C-D. Color (immature): 145A-B.

D. *Reproductive organs.*—Androecium: Present disc florets only; scant pollen. Gynoecium: Present both ray and disc florets.

II Plant:

A. *General appearance.*—Height: Short. Branching pattern: Semi-spreading.

B. *Foliage.*—Color (abaxial): 147A. Color (adaxial): 147B. Shape: Deeply lobed. Moderately serrated.

CHART A

COMPARISON OF SIREN AND CIRBRONZE

| CULTIVAR | RAY FLORET COLOR | CAPITULUM FORM AND TYPE | BRANCHING PATTERN | DIAMETER ACROSS FACE OF CAPITULUM |
|---|---|---|---|---|
| SIREN | DEEP ORANGE | FLAT DAISY | SEMI-SPREADING | 7 to 8 cm. |
| CIRBRONZE | MEDIUM BRONZE | FLAT DAISY | SEMI-SPREADING | 5.5 to 7.5 cm. |

CHART A-continued

COMPARISON OF SIREN AND CIRBRONZE

| CULTIVAR | PLANT HEIGHT | FLOWERING RESPONSE PERIOD | TEMPERATURE TOLERANCE | POLLEN |
|---|---|---|---|---|
| SIREN | SHORT 25 to 35 cm. | 7-8 WEEKS | 13 C UNIFORM 24, 38 C UNIFORM COLOR DULLS | SCANT |
| CIRBRONZE | MEDIUM 30 to 45 cm. | 9 WEEKS | 13 C UNEVEN 24, 38 C SLOW COLOR DULLS | ABUNDANT |

COMPARISONS MADE OF PLANTS GROWN AS PINCHED SPRAY POT MUMS IN SALINAS, CALIFORNIA AND LEAMINGTON, ONTARIO, CANADA

I claim:

1. A new and distinct cultivar of *Chrysanthemum morifolium,* Ramat., plant named Siren, as described and illustrated, particularly characterized as to uniqueness by the combined characteristics of flat capitulum form; daisy capitulum type; deep orange ray floret color; diameter across face of capitulum ranging from 7 to 8 cm. at maturity; uniform seven to eight week flowering response; short plant height; semi-spreading branching pattern; tolerance of both low winter 13° C. and high summer 24° C. to 38° C. temperatures for bud initiation and flower development.

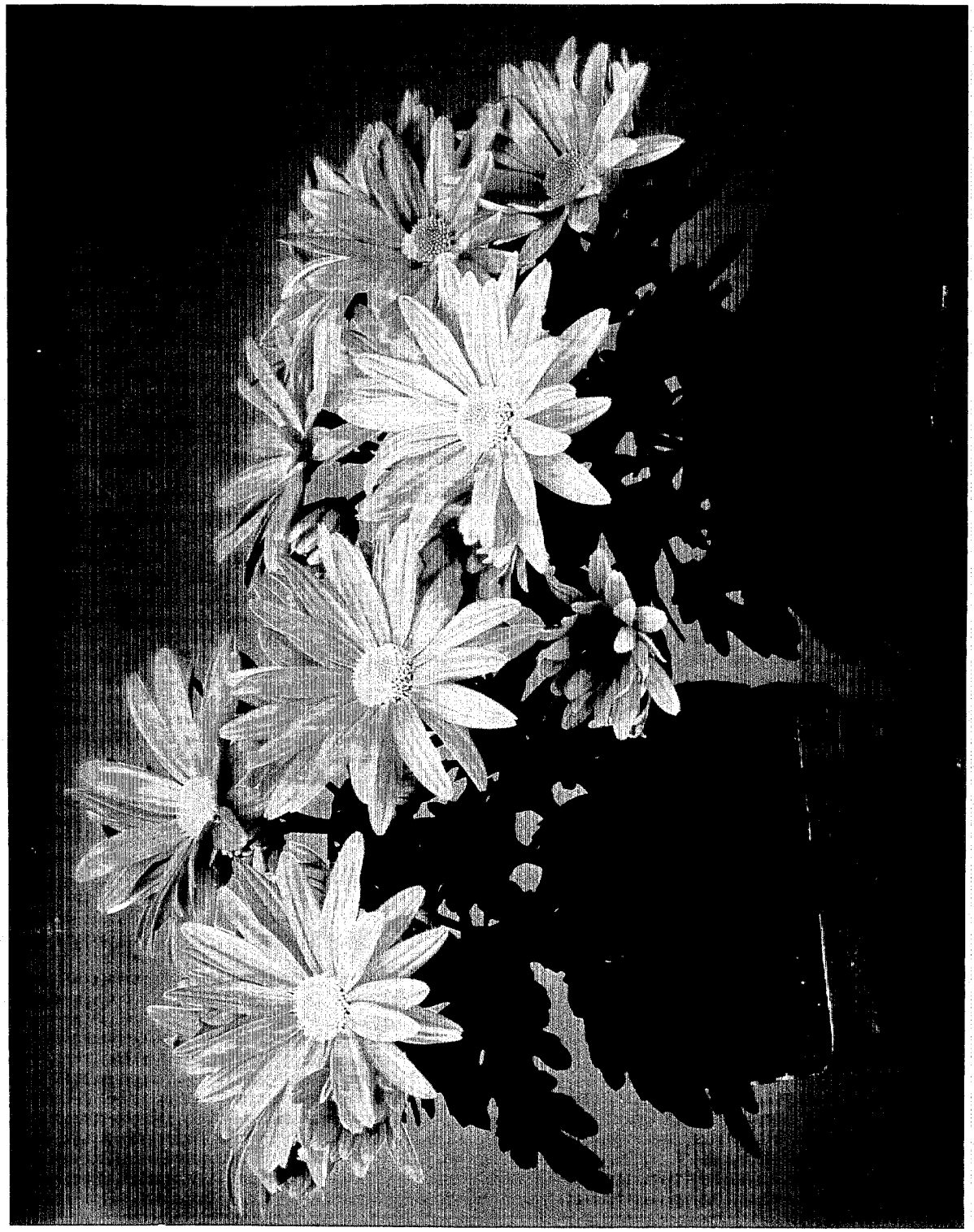

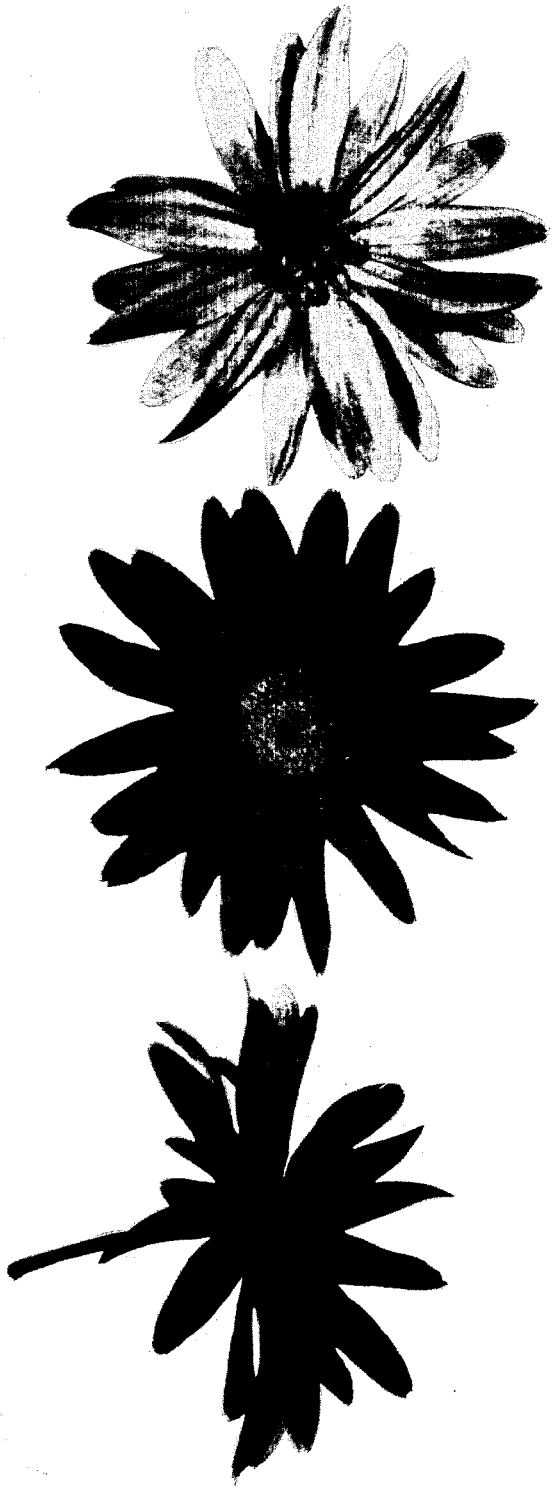

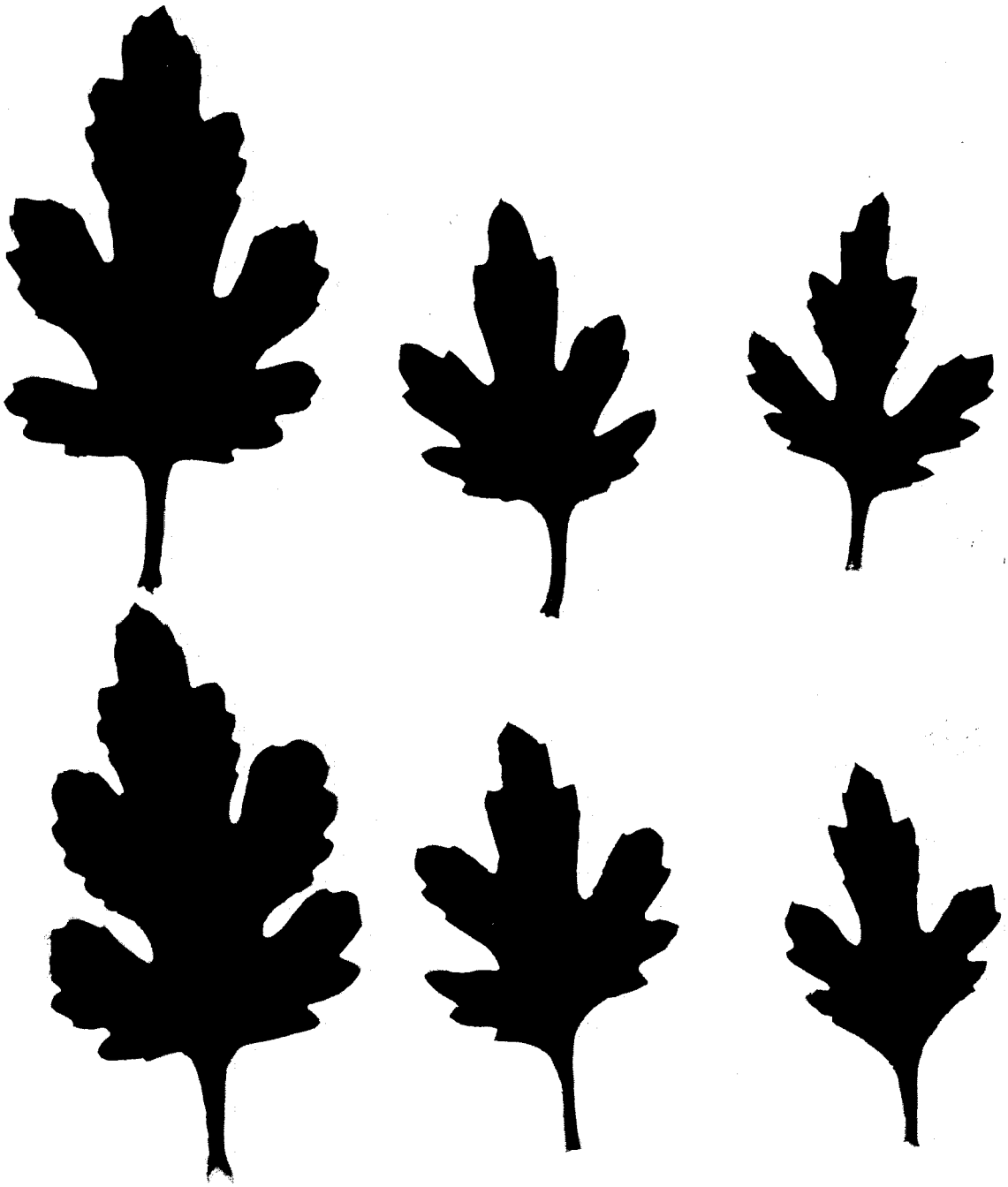

* * * * *